(12) United States Patent
Luenser

(10) Patent No.: US 9,186,860 B2
(45) Date of Patent: Nov. 17, 2015

(54) VAPORIZER KIT FOR TOBACCO, MEDICATIONS, AND THE LIKE

(71) Applicant: Carl D. Luenser, Alsip, IL (US)

(72) Inventor: Carl D. Luenser, Alsip, IL (US)

( * ) Notice: Subject to any disclaimer, the term of this patent is extended or adjusted under 35 U.S.C. 154(b) by 291 days.

(21) Appl. No.: 13/751,685

(22) Filed: Jan. 28, 2013

(65) Prior Publication Data

US 2014/0209104 A1    Jul. 31, 2014

(51) Int. Cl.
*A24F 47/00* (2006.01)
*B31D 5/04* (2006.01)
*A61M 15/06* (2006.01)
*A61M 11/04* (2006.01)

(52) U.S. Cl.
CPC ............... *B31D 5/04* (2013.01); *A24F 47/006* (2013.01); *A61M 11/045* (2014.02); *A61M 11/048* (2014.02); *A61M 15/06* (2013.01); *A61M 2205/366* (2013.01); *A61M 2205/3653* (2013.01)

(58) Field of Classification Search
USPC ............. 126/9 R; 206/85–138, 242–276, 206/521–524, 583–594
See application file for complete search history.

(56) References Cited

U.S. PATENT DOCUMENTS

| 3,653,583 | A | * | 4/1972 | Meyer ............................. 383/26 |
| 4,141,369 | A | | 2/1979 | Burruss |
| 4,230,224 | A | * | 10/1980 | Weeks ............................. 206/87 |
| 4,508,095 | A | * | 4/1985 | Bloechel ....................... 126/9 R |
| 4,712,569 | A | * | 12/1987 | Baier ............................ 131/328 |
| 4,847,469 | A | | 7/1989 | Hofmann et al. |
| 5,104,235 | A | | 4/1992 | Bronstrup et al. |
| 5,564,442 | A | | 10/1996 | MacDonald et al. |
| 5,809,989 | A | * | 9/1998 | Nelson .......................... 126/544 |
| 6,761,164 | B2 | | 7/2004 | Amirpour et al. |
| 6,835,437 | B2 | * | 12/2004 | Goers et al. ................... 428/131 |
| 7,005,121 | B2 | | 2/2006 | Rabinowitz et al. |
| 7,070,766 | B2 | | 7/2006 | Rabinowitz et al. |
| 7,090,830 | B2 | | 8/2006 | Hale et al. |
| 7,981,401 | B2 | | 7/2011 | Every et al. |
| 2003/0047471 | A1 | * | 3/2003 | Brizzi ........................... 206/273 |

(Continued)

FOREIGN PATENT DOCUMENTS

| GB | 111892 A | 12/1917 |
| RU | 1838203 A3 | 3/1993 |
| RU | 2012362 C1 | 1/1994 |

OTHER PUBLICATIONS

Enclosure defintion, http://www.merriam-webster.com/dictionary/enclosure.*

(Continued)

*Primary Examiner* — Richard Crispino
*Assistant Examiner* — Eric Yaary
(74) *Attorney, Agent, or Firm* — Richard L. Miller

(57) ABSTRACT

A knockdownable, odorless, and smokeless vaporizer kit that vaporizes materials to inhale without igniting the materials so as to reduce harmful effects of burning the materials by eliminating inhalation of combustion by-products of the materials by preventing ignition and combustion of the materials. The kit includes an enclosure and a heat source. The enclosure contains the materials. The heat source heats the enclosure to vaporize the materials contained within the enclosure without igniting the materials so as to reduce the harmful effects of burning the materials by eliminating inhalation of combustion by-products of the materials by preventing ignition and combustion of the materials.

14 Claims, 12 Drawing Sheets

(56) References Cited

U.S. PATENT DOCUMENTS

| | | | |
|---|---|---|---|
| 2003/0136705 A1* | 7/2003 | Roth | 206/582 |
| 2003/0178035 A1* | 9/2003 | Miller | 131/192 |
| 2004/0031495 A1* | 2/2004 | Steinberg | 131/194 |
| 2004/0185001 A1 | 9/2004 | Rabinowitz et al. | |
| 2008/0128300 A1* | 6/2008 | Bahar et al. | 206/242 |
| 2009/0235939 A1* | 9/2009 | Gonsalves | 131/191 |

OTHER PUBLICATIONS

Tinfoil definition, http://www.merriam-webster.com/dictionary/tinfoil.*

Improvised Foil Pot, https://www.youtube.com/watch?v=makUK9uZ5VA, Feb. 26, 2009.*

How to Smoke a Hookah, Hookah Love Blog, https://www.hookah-shisha.com/hookahlove/70-how-to-smoke-a-hookah-hookah-charcoal-and-heat-management.html, Mar. 27, 2008.*

* cited by examiner

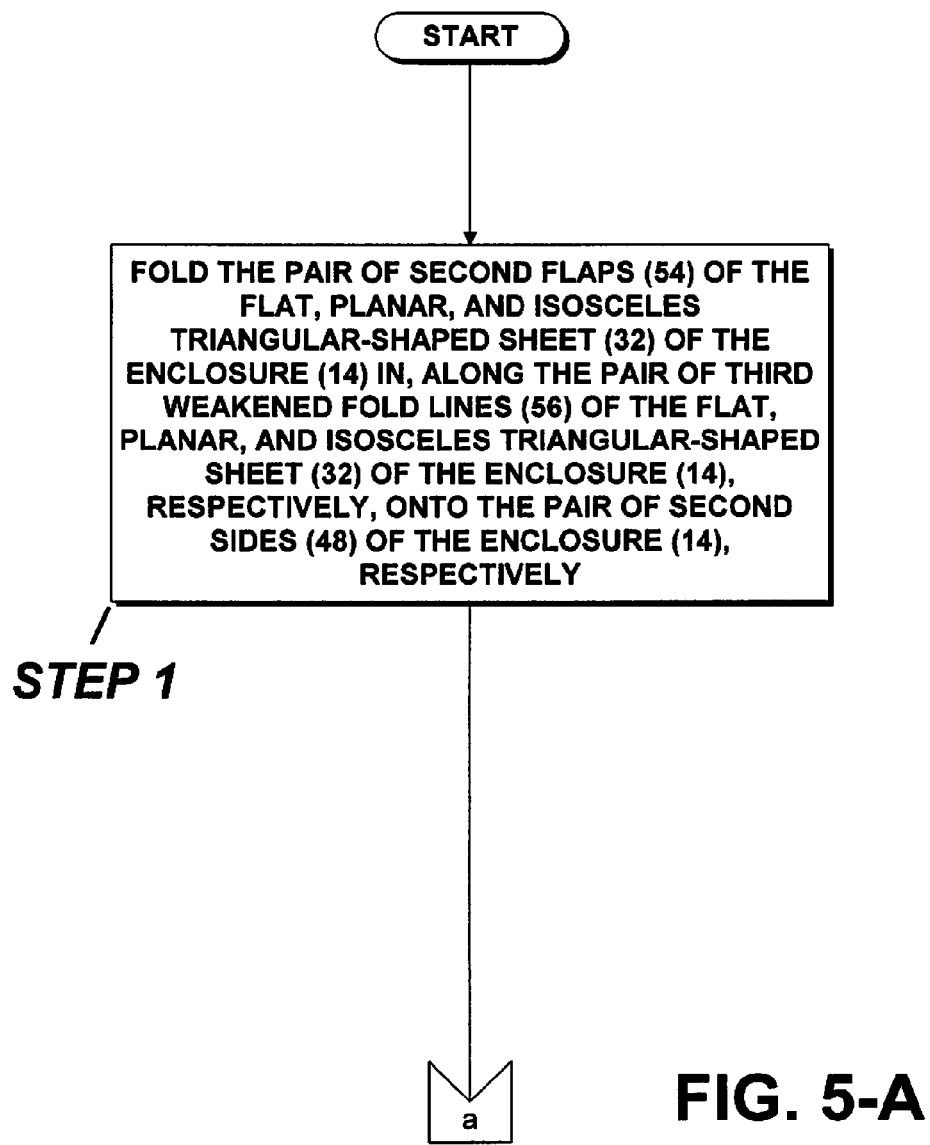
FIG. 5-A

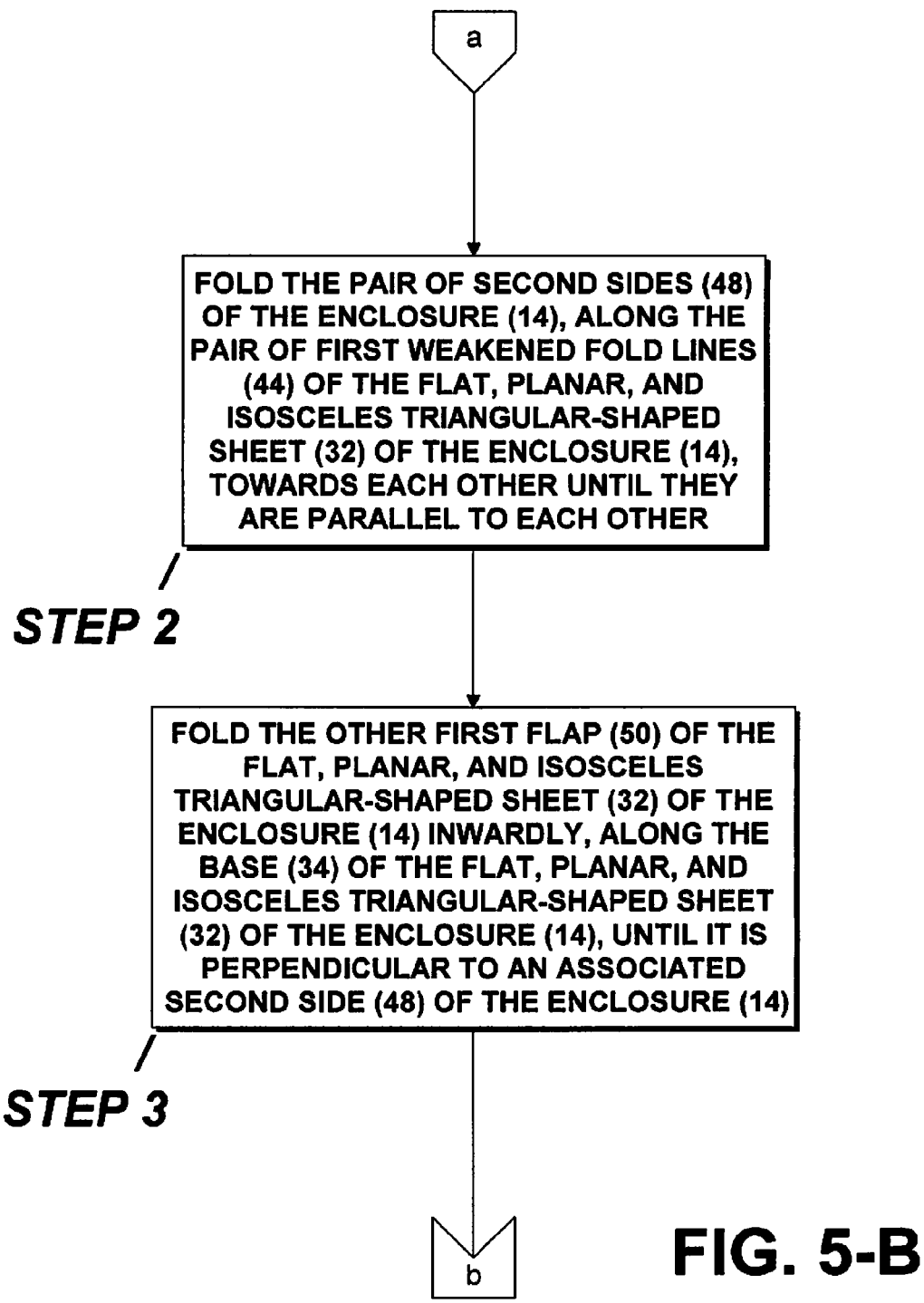
FIG. 5-B

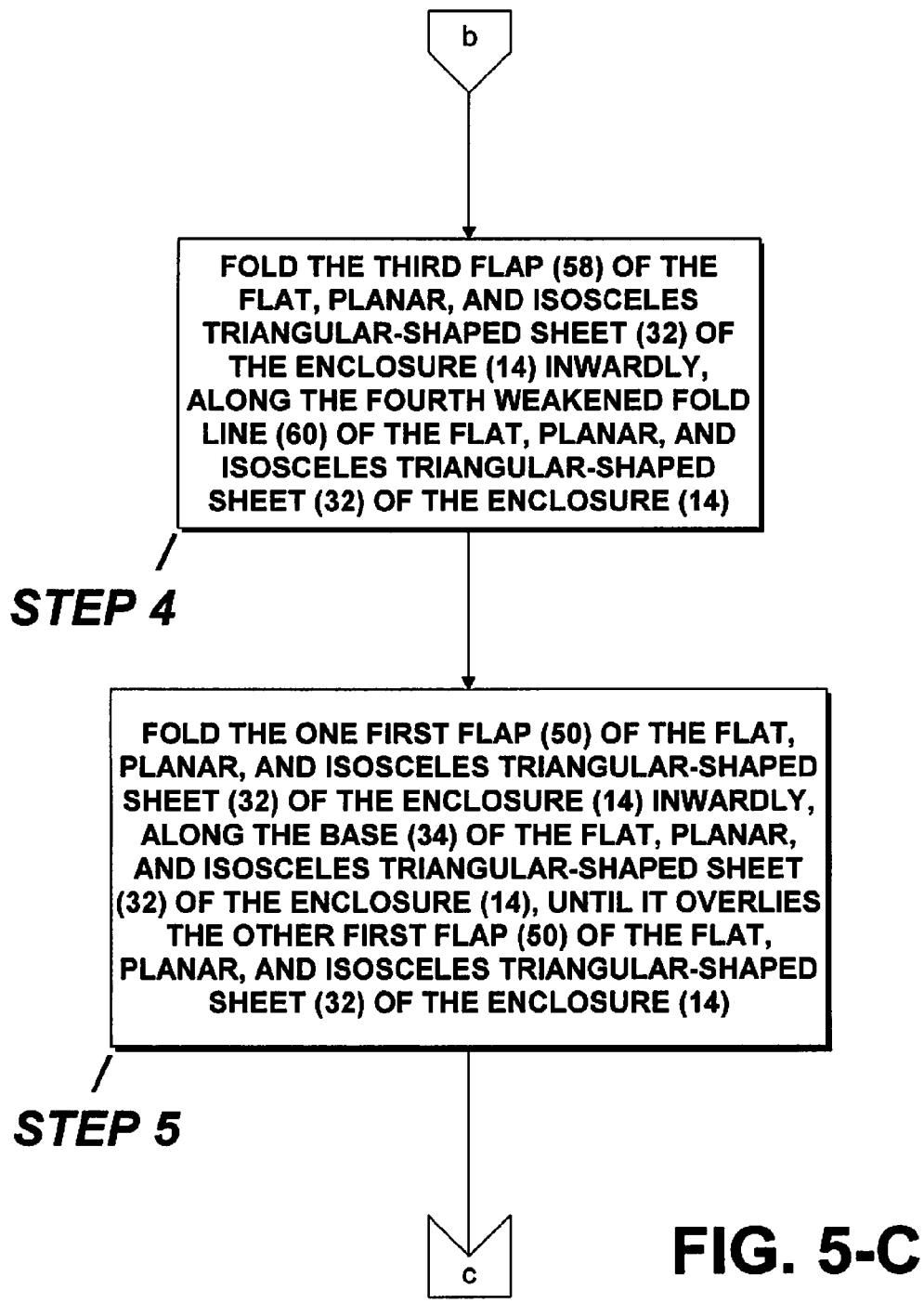
FIG. 5-C

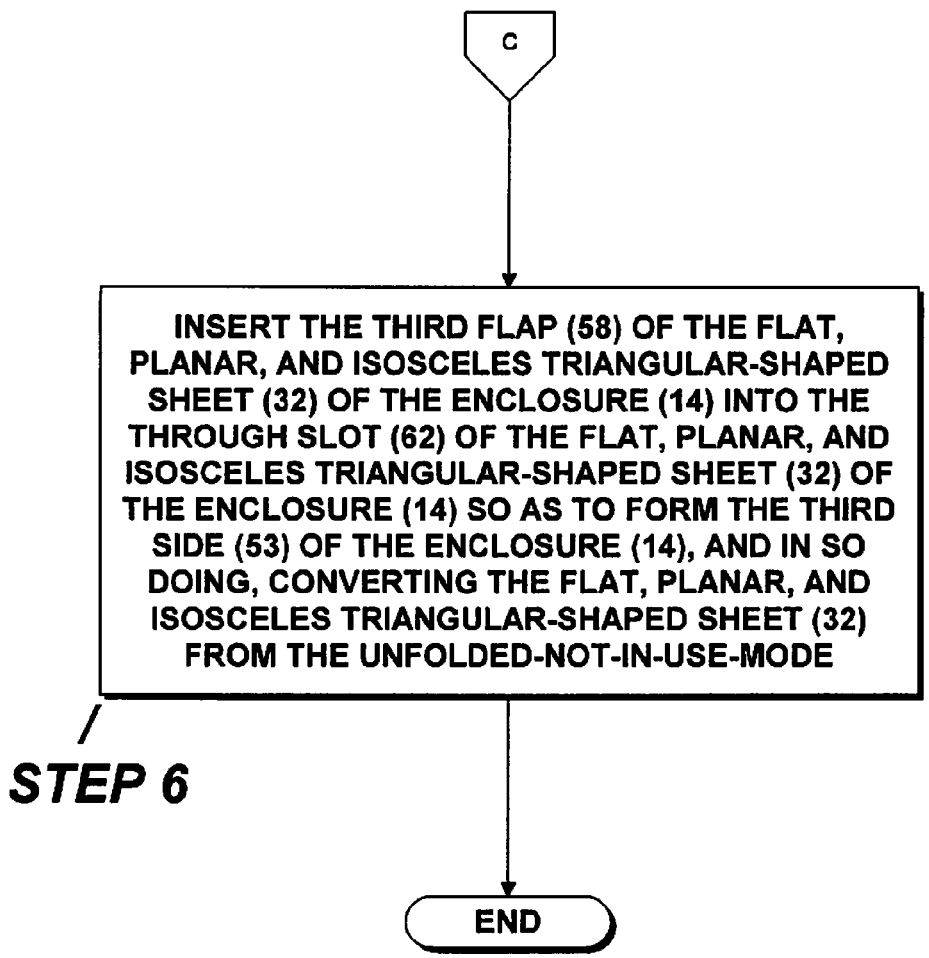
FIG. 5-D

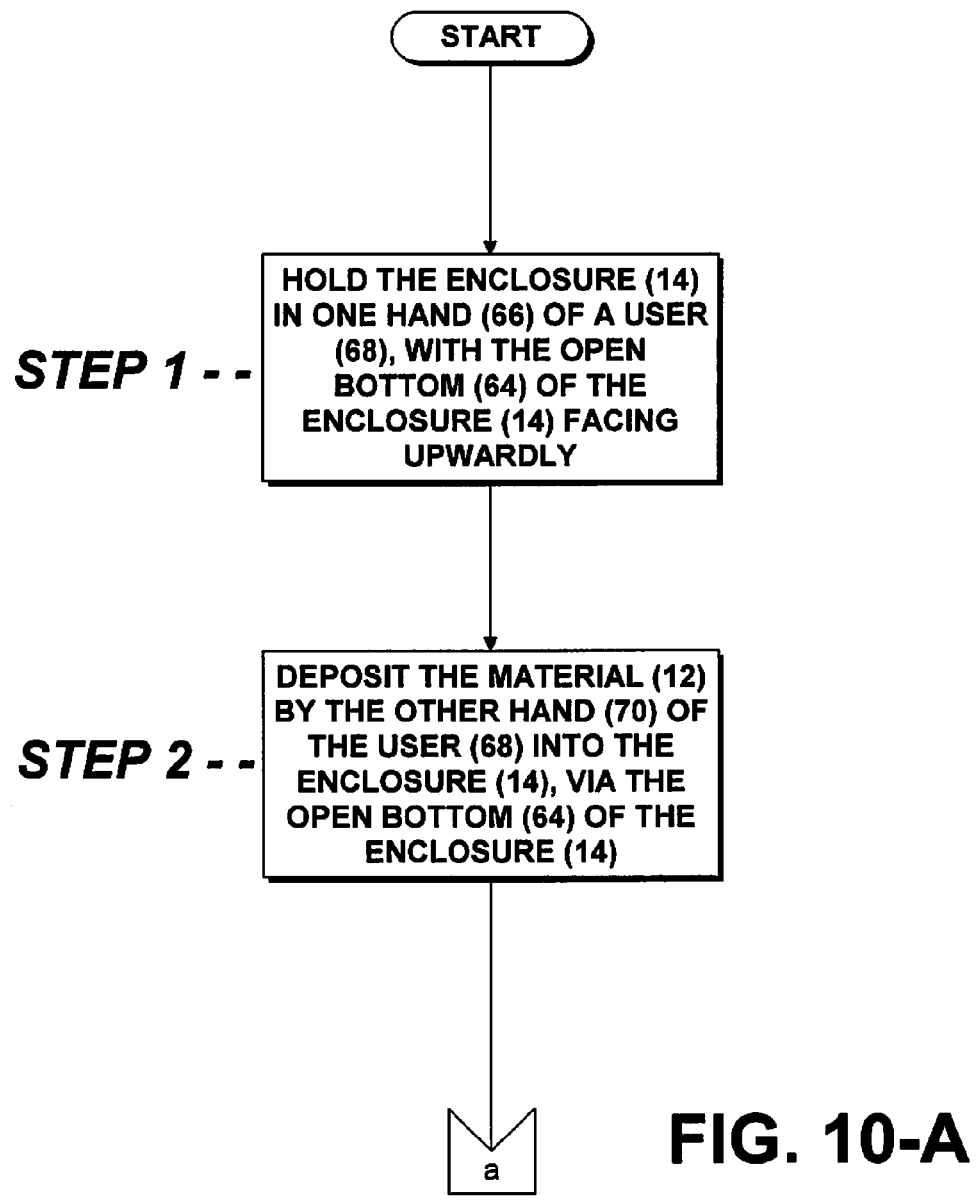
FIG. 10-A

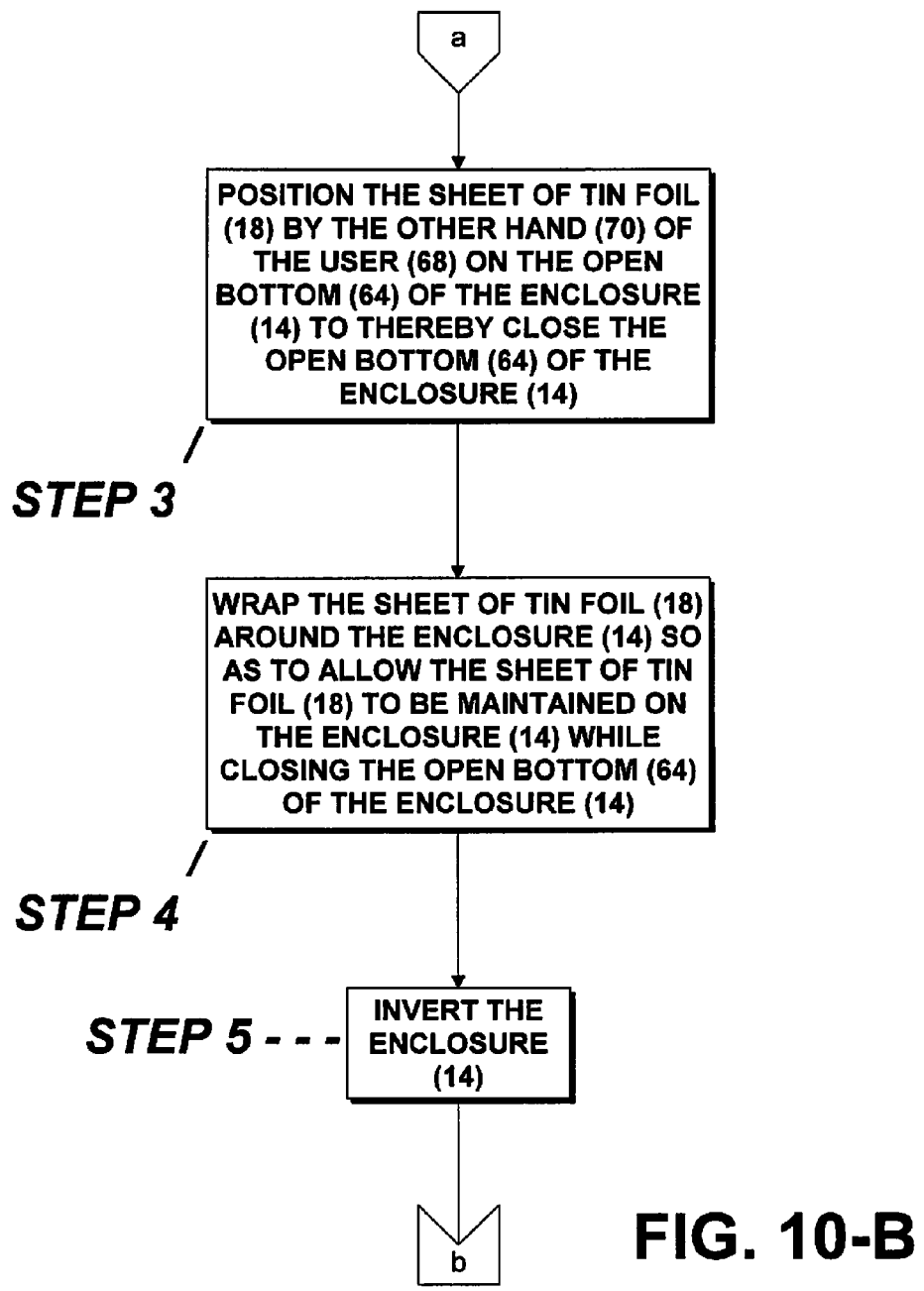
FIG. 10-B

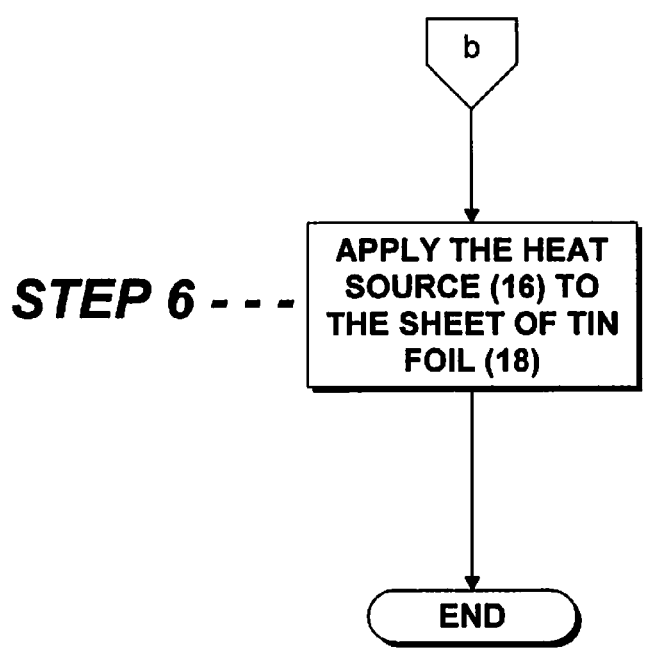
FIG. 10-C

VAPORIZER KIT FOR TOBACCO, MEDICATIONS, AND THE LIKE

1. BACKGROUND OF THE INVENTION

A. Field of the Invention

The embodiments of the present invention relate to a vaporizer, and more particularly, the embodiments of the present invention relate to a knockdownable, odorless, and smokeless vaporizer kit for vaporizing materials for inhalation without igniting the materials so as to reduce harmful effects of burning the materials by eliminating inhalation of combustion by-products of the materials by preventing ignition and combustion of the materials.

B. Description of the Prior Art

Numerous innovations for vaporizing devices have been provided in the prior art, which will be described below in chronological order to show advancement in the art, and which are incorporated in their entirety herein by reference thereto. Even though these innovations may be suitable for the specific individual purposes to which they address, nevertheless, they differ from the present invention in that they do not teach a knockdownable, odorless, and smokeless vaporizer kit for vaporizing materials for inhalation without igniting the materials so as to reduce harmful effects of burning the materials by eliminating inhalation of combustion by-products of the materials by preventing ignition and combustion of the materials.

(1) U.S. Pat. No. 4,141,369 to Burruss

U.S. Pat. No. 4,141,369—issued to Burruss on Feb. 27, 1979 in U.S. class 131 and subclass 330—teaches an electrical device for the noncombustion utilization of tobacco and other smoking materials. The device includes a canister or other appropriate container within which air is electrically heated to an appropriate temperature for volatilizing the desired components of smoking material previously inserted into a receptacle provided in a mouthpiece assembly. Volatilization takes place when the heated air is drawn through the smoking material contained in the mouthpiece assembly. The mixture of heated air and volatilized smoking material components is then drawn from the mouthpiece into the mouth and respiratory passages of the user of the device.

(2) U.S. Pat. No. 4,847,469 to Hofmann et al.

U.S. Pat. No. 4,847,469—issued to Hofmann et al. on Jul. 11, 1989 in U.S. class 392 and subclass 397—teaches a vaporizing apparatus that delivers precisely controlled, substantially continuous, and monitored vapor flows for uses, such as in plasma enhanced vapor deposition. The vaporizing apparatus includes a fluid passageway along which are a pumping device, a vaporizing device, and a flowing device, and all in fluid communication with the passageway. The vaporizing device vaporizes liquid pumped from the pumping device and includes a heat sink layer, a heated layer, and a portion of the passageway sandwiched therebetween. The vaporizing apparatus sustains a flow of organosilicon vapor at a flow rate of about 1 to about 100 SCCM for as long as desired.

(3) U.S. Pat. No. 5,564,442 to MacDonald et al.

U.S. Pat. No. 5,564,442—issued to MacDonald et al. on Oct. 15, 1996 in U.S. class 131 and subclass 194—teaches a nicotine vaporizer including a housing with a battery compartment size for a pair of AA dry cells, and a compartment for containing tobacco. A lower portion of the housing has a hole for passing tobacco into a firebox cavity arranged there below and shiftable from a tobacco receiving to a tobacco burning position. Electric coil apparatus is set in the firebox cavity and energized to bring the tobacco to combustion temperature. A mouthpiece-equipped suction tube extends into the housing so that as air is withdrawn through the suction tube with the coil energized, the tobacco combusts as to the microcharge contained in the firebox cavity. The microcharge of tobacco is of a volume that no more smoke is created than is processed by the lungs in one breath.

(4) U.S. Pat. No. 6,761,164 to Amirpour et al.

U.S. Pat. No. 6,761,164—issued to Amirpour et al. on Jul. 13, 2004 in U.S. class 128 and subclass 203.26—teaches a fire-resistant housing forming a heat generating compartment having an access opening and at least one elongated heating element that is coupled to a support element in the compartment to position a second end of the heating element proximate the access opening for vaporizing an herbal sample placed in close proximity thereof. The second end is further positioned at a height equal to or less than the height between the first end and an underlying support surface. A connector is included to electrically connect the heating element to a power source for energizing the heating element.

(5) U.S. Pat. No. 7,005,121 to Rabinowitz et al.

U.S. Pat. No. 7,005,121—issued to Rabinowitz et al. on Feb. 28, 2006 in U.S. class 424 and subclass 45—teaches a delivery of a migraine headache drug through an inhalation route. Specifically, it relates to aerosols containing a migraine headache drug that are used in inhalation therapy. In a method aspect, a migraine headache drug is administered to a patient through an inhalation route. The method includes heating a composition that is a migraine headache drug to form a vapor, and allowing the vapor to cool thereby forming a condensation aerosol including particles of aerosol-including particles with less than 5% drug degradation products. In a kit aspect, a kit for delivering a migraine headache drug through an inhalation route includes a thin coating of an a migraine drug composition, and a device for dispensing the thin coating as a condensation aerosol.

(6) U.S. Pat. No. 7,070,766 to Rabinowitz et al.

U.S. Pat. No. 7,070,766—issued to Rabinowitz et al. on Jul. 4, 2006 in U.S. class 424 and subclass 45—teaches the delivery of physiologically active compounds through an inhalation route. Specifically, it relates to aerosols containing physiologically active compounds that are used in inhalation therapy. In a method aspect, a physiologically active compound is delivered to a patient through an inhalation route. The method includes heating a composition including a physiologically active compound to form a vapor; and allowing the vapor to cool thereby forming a condensation aerosol including particles with less than 5% physiologically active compound degradation products. In a kit aspect, a kit for delivering a physiologically active compound through an inhalation route, which includes a thin coating of a physiologically active compound composition, and a device for dispensing the thin coating as a condensation aerosol.

(7) U.S. Pat. No. 7,090,830 to Hale et al.

U.S. Pat. No. 7,090,830—issued to Hale et al. on Aug. 15, 2006 in U.S. class 424 and subclass 45—teaches condensation aerosols for the treatment of disease and/or intermittent or acute conditions. The condensation aerosols have little or no pyrolysis degradation products and are characterized by having an MMAD of between 1 3 microns. The aerosols are made by rapidly heating a substrate coated with a thin film of drug having a thickness of between 0.05 and 20 .mu.m, while passing a gas over the film, to form particles of a desirable particle size for inhalation. Kits include a drug and a device for producing a condensation aerosol. The device contained in the kit typically has an element for heating the drug, which is coated as a film on the substrate and contains a therapeutically effective dose of a drug when the drug is administered in aerosol form, and an element allowing the vapor to cool to form an aerosol. Also taught are methods for using the aerosols and kits.

(8) U.S. Pat. No. 7,981,401 to Every et al.

U.S. Pat. No. 7,981,401—issued to Every et al. on Jul. 19, 2011 in U.S. class 424 and subclass 43—teaches diuretic condensation aerosols and methods of making and using them. Kits for delivering a condensation aerosol are also taught. The diuretic aerosols typically include diuretic condensation aerosol particles that include a diuretic compound. In some variations, the diuretic compound is selected from the group including bumetanide, ethacrynic acid, furosemide, muzolimine, spironolactone, torsemide, triamterene, tripamide, BG 9928, and BG 9719. Methods of treating edema using the aerosols are also taught. In general, the methods typically includes the step of administering a therapeutically effective amount of diuretic condensation aerosol to a person with edema. The diuretic condensation aerosol is administered in a single inhalation or is administered in more than one inhalation. Methods of forming a diuretic condensation aerosol are also taught. The methods typically include the steps of providing a diuretic composition, vaporizing the composition to form a vapor, and then condensing the diuretic composition vapor.

It is apparent that numerous innovations for vaporizing devices have been provided in the prior art, which are adapted to be used. Furthermore, even though these innovations may be suitable for the specific individual purposes to which they address, nevertheless, they would not be suitable for the purposes of the embodiments of the present invention as heretofore described, namely, a knockdownable, odorless, and smokeless vaporizer kit for vaporizing materials for inhalation without igniting the materials so as to reduce harmful effects of burning the materials by eliminating inhalation of combustion by-products of the materials by preventing ignition and combustion of the materials.

2. SUMMARY OF THE INVENTION

Thus, an object of the embodiments of the present invention is to provide a knockdownable, odorless, and smokeless vaporizer kit for vaporizing materials for inhalation without igniting the materials so as to reduce harmful effects of burning the materials by eliminating inhalation of combustion by-products of the materials by preventing ignition and combustion of the materials, which avoids the disadvantages of the prior art.

Briefly stated, another object of the embodiments of the present invention is to provide a knockdownable, odorless, and smokeless vaporizer kit that vaporizes materials to inhale without igniting the materials so as to reduce harmful effects of burning the materials by eliminating inhalation of combustion by-products of the materials by preventing ignition and combustion of the materials. The kit includes an enclosure and a heat source. The enclosure contains the materials. The heat source heats the enclosure to vaporize the materials contained within the enclosure without igniting the materials so as to reduce the harmful effects of burning the materials by eliminating inhalation of combustion by-products of the materials by preventing ignition and combustion of the materials.

The novel features considered characteristic of the embodiments of the present invention are set forth in the appended claims. The embodiments of the present invention themselves, however, both as to their construction and to their method of operation together with additional objects and advantages thereof will be best understood from the following description of the specific embodiments when read and understood in connection with the accompanying figures of the drawing.

3. BRIEF DESCRIPTION OF THE FIGURES OF THE DRAWING

The figures of the drawing are briefly described as follows:

FIG. 1 is a diagrammatic perspective view of the knockdownable, odorless, and smokeless vaporizer kit of the embodiments of the present invention vaporizing materials for inhalation without igniting the materials so as to reduce harmful effects of burning the materials by eliminating inhalation of combustion by-products of the materials by preventing ignition and combustion of the materials and being activated by a hotplate;

FIG. 1A is a diagrammatic perspective view of the knockdownable, odorless, and smokeless vaporizer kit of the embodiments of the present invention for vaporizing materials for inhalation without igniting the materials so as to reduce harmful effects of burning the materials by eliminating inhalation of combustion by-products of the materials by preventing ignition and combustion of the materials and being activated by a cigarette lighter;

FIG. 5A-5D are a flowchart of the method of converting the flat, planar, and isosceles triangular-shaped sheet of the enclosure from the unfolded-not-in-use-mode thereof to the folded-in-use-mode thereof;

Figure 1:
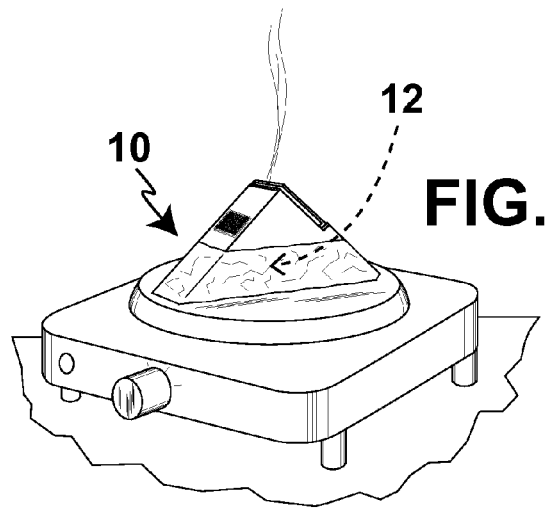
FIG. 1B is a diagrammatic perspective view of the knockdownable, odorless, and smokeless vaporizer kit of the embodiments of the present invention shown in FIG. 1A assembled and having the cigarette lighter replaceably attached thereto.
Figure 7:
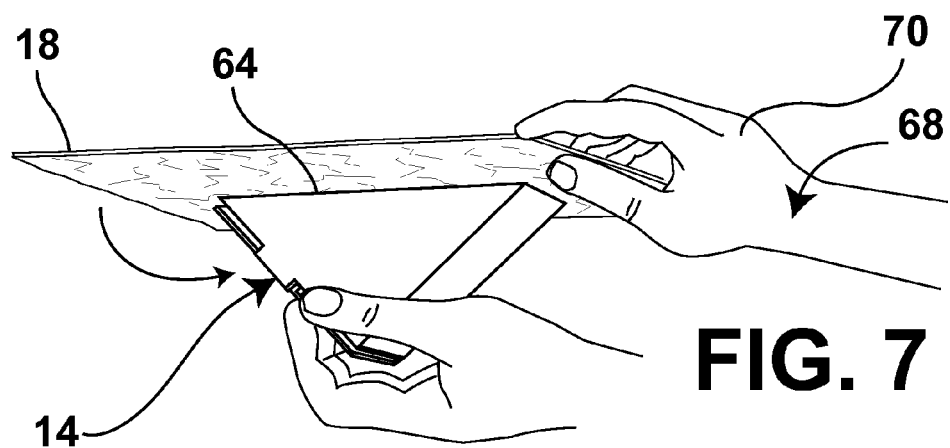
FIG. 7 is a diagrammatic perspective view of the assembled enclosure of the knockdownable, odorless, and smokeless vaporizer kit of the embodiments of the present invention shown in FIG. 6 and being closed by a foil sheet of the knockdownable, odorless, and smokeless vaporizer kit of the embodiments of the present invention.
Figure 8:
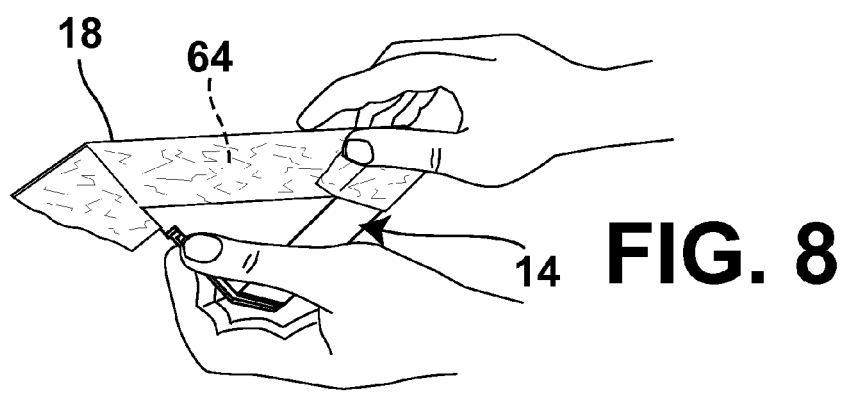
Figure 9:
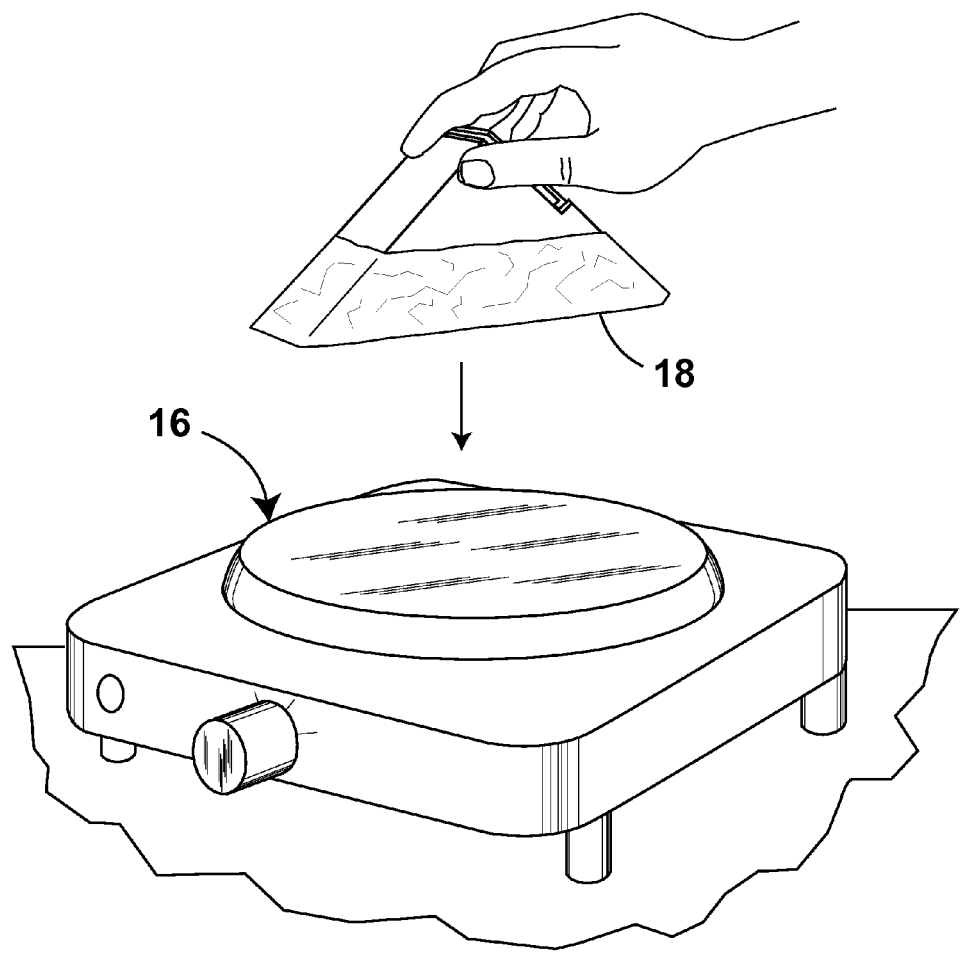

FIG. 8 is a diagrammatic perspective view of the assembled enclosure of the knockdownable, odorless, and smokeless vaporizer kit of the embodiments of the present invention shown in FIG. 7 and having the foil sheet of the knockdownable, odorless, and smokeless vaporizer kit of the embodiments of the present invention folded around the enclosure of the knockdownable, odorless, and smokeless vaporizer kit of the embodiments of the present invention ready for use;

FIG. 9 is an enlarged and exploded diagrammatic perspective view of the ready to use knockdownable, odorless, and smokeless vaporizer kit of the embodiments of the present invention being placed on a hotplate heat source as shown in FIG. 1; and FIGS. 10A-10C are a flow chart of the method of using the knockdownable, odorless, and smokeless vaporizer kit.

4. LIST OF REFERENCE NUMERALS UTILIZED IN THE FIGURES OF THE DRAWING

A. Introductory.
10 knockdownable, odorless, and smokeless vaporizer kit of embodiments of present invention for vaporizing materials 12 for inhalation without igniting materials 12 so as to reduce harmful effects of burning materials 12 by eliminating inhalation of combustion by-products of materials 12 by preventing ignition and combustion of materials 12
12 materials
B. Components of Knockdownable, Odorless, and Smokeless Vaporizer Kit 10.
14 enclosure for containing material 12
16 heat source for vaporizing materials 12 contained within enclosure 14 without igniting materials 12 so as to reduce harmful effects of burning materials 12 by eliminating inhalation of combustion by-products of materials 12 by preventing ignition and combustion of materials 12
18 sheet of tin foil
20 mating portions of hook and loop fasteners
22 secondary bag
24 primary bag
26 closure of primary bag 24
28 pull cord of closure 26 of primary bag 24
30 carrying handles of pull cord 28 of closure 26 of primary bag 24
32 flat, planar, and isosceles triangular-shaped sheet of enclosure 14
34 base of flat, planar, and isosceles triangular-shaped sheet 32 of enclosure 14
36 pair of equal sides of flat, planar, and isosceles triangular-shaped sheet 32 of enclosure 14
38 truncated apex of flat, planar, and isosceles triangular-shaped sheet 32 of enclosure 14
40 pair of ends of base 34 of flat, planar, and isosceles triangular-shaped sheet 32 of enclosure 14
42 pair of ends of truncated apex 38 of flat, planar, and isosceles triangular-shaped sheet 32 of enclosure 14
44 pair of first weakened fold lines of flat, planar, and isosceles triangular-shaped sheet 32 of enclosure 14
46 first side of enclosure 14 when enclosure 14 is in folded-in-use-mode thereof
48 pair of second sides of enclosure 14 when enclosure 14 is in folded-in-use-mode thereof
50 pair of first flaps of flat, planar, and isosceles triangular-shaped sheet 32 of enclosure 14
52 pair of second weakened fold lines of flat, planar, and isosceles triangular-shaped sheet 32 of enclosure 14
53 third side of enclosure 14
54 pair of second flaps of flat, planar, and isosceles triangular-shaped sheet 32 of enclosure 14
56 pair of third weakened fold lines of flat, planar, and isosceles triangular-shaped sheet 32 of enclosure 14
58 third flap of flat, planar, and isosceles triangular-shaped sheet 32 of enclosure 14
60 fourth weakened fold line of flat, planar, and isosceles triangular-shaped sheet 32 of enclosure 14
62 through slot of flat, planar, and isosceles triangular-shaped sheet 32 of enclosure 14
C. Method of Converting Flat, Planar, and Isosceles Triangular-shaped Sheet from Unfolded-not-in-use-mode Thereof to Folded-in-use-mode Thereof.
64 open bottom of enclosure 14
D. Method of Using Knockdownable, Odorless, and Smokeless Vaporizer Kit 10.
66 one hand of user 68
68 user
70 other hand of user 68

5. DETAILED DESCRIPTION OF THE PREFERRED EMBODIMENTS

A. Introductory.
Referring now to the figures, in which like numerals indicate like parts, and particularly to FIGS. 1, 1A, and 1B, which are, respectively, a diagrammatic perspective view of the knockdownable, odorless, and smokeless vaporizer kit of the embodiments of the present invention vaporizing materials for inhalation without igniting the materials so as to reduce harmful effects of burning the materials by eliminating inhalation of combustion by-products of the materials by preventing ignition and combustion of the materials and being activated by a hotplate, a diagrammatic perspective view of the knockdownable, odorless, and smokeless vaporizer kit of the embodiments of the present invention for vaporizing materials for inhalation without igniting the materials so as to reduce harmful effects of burning the materials by eliminating inhalation of combustion by-products of the materials by preventing ignition and combustion of the materials and being activated by a cigarette lighter, and a diagrammatic perspective view of the knockdownable, odorless, and smokeless vaporizer kit of the embodiments of the present invention shown in FIG. 1A assembled and having the cigarette lighter replaceably attached thereto, the knockdownable, odorless, and smokeless vaporizer kit of the embodiments of the present invention is shown generally at 10 for vaporizing materials 12 for inhalation without igniting the materials 12 so as to reduce harmful effects of burning the materials 12 by eliminating inhalation of combustion by-products of the materials 12 by preventing ignition and combustion of the materials 12.

B. Components of the Knockdownable, Odorless, and Smokeless Vaporizer Kit 10.

Figure 1A:
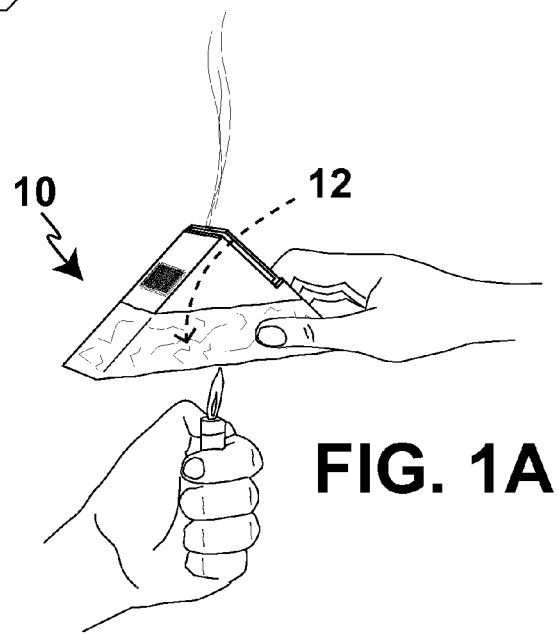
Figure 1B:
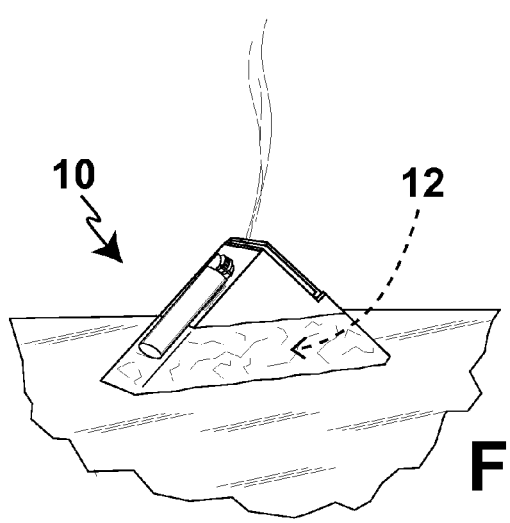

The components of the knockdownable, odorless, and smokeless vaporizer kit 10 can best be seen in FIG. 2, which is an exploded diagrammatic elevational view of the knockdownable, odorless, and smokeless vaporizer kit of the embodiments of the present invention shown assembled in FIGS. 1, 1A, and 1B, an as such, will be discussed with referenced thereto.

The knockdownable, odorless, and smokeless vaporizer kit 10 comprises an enclosure 14 and a heat source 16. The enclosure 14 is for containing the materials 12. The heat source 16 heats the enclosure 14 for vaporizing the materials 12 contained within the enclosure 14 without igniting the materials 12 so as to reduce the harmful effects of burning the materials 12 by eliminating inhalation of combustion by-products of the materials 12 by preventing ignition and combustion of the materials 12.

The knockdownable, odorless, and smokeless vaporizer kit 10 further comprises a sheet of tin foil 18.

The sheet of tin foil 18 is attached to the enclosure 14 and interfaces with the heat source 16 to heat the enclosure 14 for vaporizing the materials 12 contained within the enclosure 14 without igniting the materials 12 so as to reduce the harmful effects of burning the materials 12 by eliminating inhalation of combustion by-products of the materials 12 by preventing ignition and combustion of the materials 12.

The knockdownable, odorless, and smokeless vaporizer kit 10 further comprises mating portions of hook and loop fasteners 20.

The mating portions of hook and loop fasteners 20 replaceably attach the heat source 16 to the enclosure 14 when the heat source 16 is not in use.

The knockdownable, odorless, and smokeless vaporizer kit 10 further comprises a secondary bag 22.

The secondary bag 22 replaceably contains the mating portions of hook and loop fasteners 20 when the mating portions of hook and loop fasteners 20 are not in use.

The knockdownable, odorless, and smokeless vaporizer kit 10 further comprises a primary bag 24.

The primary bag 24 carries the enclosure 14, the heat source 16, the sheet of tin foil 18, and the secondary bag 22 prior to assembling the knockdownable, odorless, and smokeless vaporizer kit 10.

The primary bag 24 has a closure 26.

The closure 26 of the primary bag 24 is, preferably, a pull cord 28, but is not limited to that.

The pull cord 28 of the closure 26 of the primary bag 24 doubles as carrying handles 30.

It is to be understood that the knockdownable, odorless, and smokeless vaporizer kit 10 can comprise of more than one enclosure 14, more than one sheet of tin foil 18, and more than one mating portions of hook and loop fasteners 20, without departing in any way from the spirit of the embodiments of the present invention.

The enclosure 14 has an unfolded-not-in-use-mode and a folded-in-use-mode.

In the unfolded-not-in-use-mode of the enclosure 14, the enclosure 14 is a flat, planar, and isosceles triangular-shaped sheet 32.

The flat, planar, and isosceles triangular-shaped sheet 32 of the enclosure 14 has a base 34, a pair of equal sides 36, and a truncated apex 38.

The base 34 of the flat, planar, and isosceles triangular-shaped sheet 32 of the enclosure 14 is straight, and has a pair of ends 40.

The truncated apex 38 of the flat, planar, and isosceles triangular-shaped sheet 32 of the enclosure 14 is parallel to, and shorter than, the base 34 of the flat, planar, and isosceles triangular-shaped sheet 32 of the enclosure 14, and has a pair of ends 42.

A pair of first weakened fold lines 44 depend from the pair of ends 42 of the truncated apex 38 of the flat, planar, and isosceles triangular-shaped sheet 32 of the enclosure 14, respectively, to the base 34 of the flat, planar, and isosceles triangular-shaped sheet 32 of the enclosure 14.

The pair of first weakened fold lines 44 of the flat, planar, and isosceles triangular-shaped sheet 32 of the enclosure 14 define therebetween a first side 46 of the enclosure 14 when the enclosure 14 is in the folded-in-use-mode thereof.

The pair of first weakened fold lines 44 of the flat, planar, and isosceles triangular-shaped sheet 32 of the enclosure 14 and the pair of equal sides 36 of the flat, planar, and isosceles triangular-shaped sheet 32 of the enclosure 14, respectively, define a pair of second sides 48 of the enclosure 14 when the enclosure 14 is in the folded-in-use-mode thereof.

The flat, planar, and isosceles triangular-shaped sheet 32 of the enclosure 14 further has a pair of first flaps 50.

The pair of first flaps 50 of the flat, planar, and isosceles triangular-shaped sheet 32 of the enclosure 14 are rectangular-shaped.

The pair of first flaps 50 of the flat, planar, and isosceles triangular-shaped sheet 32 of the enclosure 14 depend coplanarly from the base 34 of the flat, planar, and isosceles triangular-shaped sheet 32 of the enclosure 14, at a pair of second weakened fold lines 52, and extend from the pair of ends 40 of the base 34 of the flat, planar, and isosceles triangular-shaped sheet 32 of the enclosure 14 to the pair of first weakened fold lines 44 of the flat, planar, and isosceles triangular-shaped sheet 32 of the enclosure 14, respectively.

The pair of first flaps 50 of the flat, planar, and isosceles triangular-shaped sheet 32 of the enclosure 14 form a third side 53 of the enclosure 14 when the enclosure 14 is in the folded-in-use-mode thereof.

The flat, planar, and isosceles triangular-shaped sheet 32 of the enclosure 14 further has a pair of second flaps 54.

The pair of second flaps 54 of the flat, planar, and isosceles triangular-shaped sheet 32 of the enclosure 14 are isosceles triangular-shaped.

The pair of second flaps 54 of the flat, planar, and isosceles triangular-shaped sheet 32 of the enclosure 14 extend coplanarly outwardly from the pair of equal sides 36 of the flat, planar, and isosceles triangular-shaped sheet 32 of the enclosure 14, respectively, at a pair of third weakened fold lines 56.

The flat, planar, and isosceles triangular-shaped sheet 32 of the enclosure 14 further has a third flap 58.

The third flap 58 of the flat, planar, and isosceles triangular-shaped sheet 32 of the enclosure 14 extends coplanarly outwardly from one of the first flaps 50 of the flat, planar, and isosceles triangular-shaped sheet 32 of the enclosure 14, at a fourth weakened fold line 60.

The flat, planar, and isosceles triangular-shaped sheet 32 of the enclosure 14 further has a through slot 62.

The through slot 62 of the flat, planar, and isosceles triangular-shaped sheet 32 of the enclosure 14 extends along the base 34 of the flat, planar, and isosceles triangular-shaped sheet 32 of the enclosure 14, at the other first flap 50 of the flat, planar, and isosceles triangular-shaped sheet 32 of the enclosure 14.

The flat, planar, and isosceles triangular-shaped sheet 32 of the enclosure 14 can be, but is not limited to, a corrugated protector for safeguarding picture frames and mirrors from scratches, which is sold by ULINE Shipping Supply Specialists 1-800-295-5510 (uline.com) under model number S-8474.

C. Method of Converting the Flat, Planar, and Isosceles Triangular-shaped Sheet from the Unfolded-not-in-use-mode Thereof to the Folded-in-use-mode Thereof.

Figure 2:
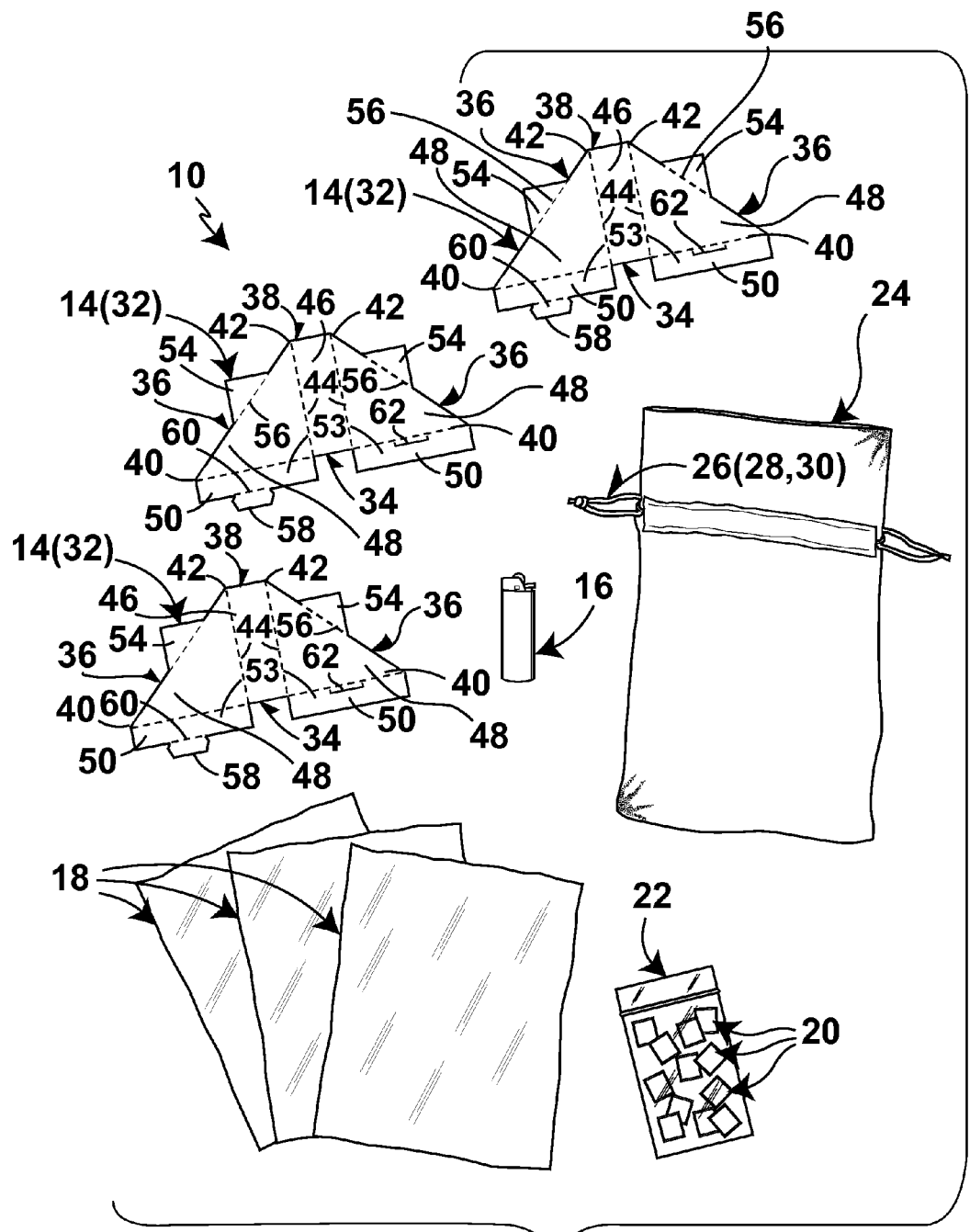
FIG. 2 is an exploded diagrammatic elevational view of the knockdownable, odorless, and smokeless vaporizer kit of the embodiments of the present invention shown assembled in FIGS. 1, 1A, and 1B.
Figure 3:
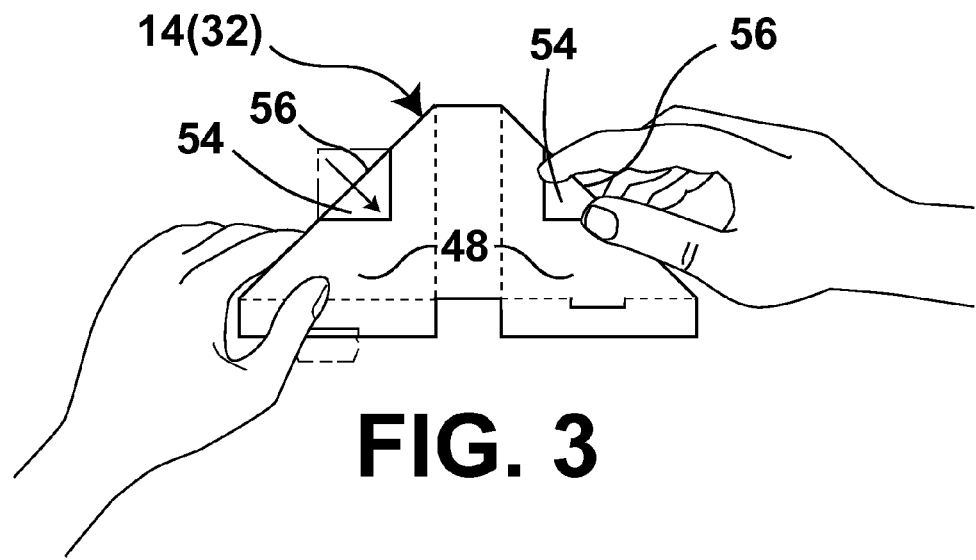
FIG. 3 is a diagrammatic front elevational view of an enclosure of the knockdownable, odorless, and smokeless vaporizer kit of the embodiments of the present invention shown in FIG. 2 and in the process of being folded for assembly.

The method of converting the flat, planar, and isosceles triangular-shaped sheet 32 from the unfolded-not-in-use-mode thereof to the folded-in-use-mode thereof can best be seen in FIGS. 3, 4, and 5A-5D, which are, respectively, a diagrammatic front elevational view of an enclosure of the knockdownable, odorless, and smokeless vaporizer kit of the embodiments of the present invention shown in FIG. 2 and in the process of being folded for assembly, a diagrammatic side elevational view of the enclosure of the knockdownable, odorless, and smokeless vaporizer kit of the embodiments of the present invention shown in FIG. 3 and in the process of being further folded for assembly, and a flowchart of the method of converting the flat, planar, and isosceles triangular-shaped sheet from the unfolded-not-in-use-mode thereof to the folded-in-use-mode thereof, and as such, will be discussed with reference thereto.

Figure 4:
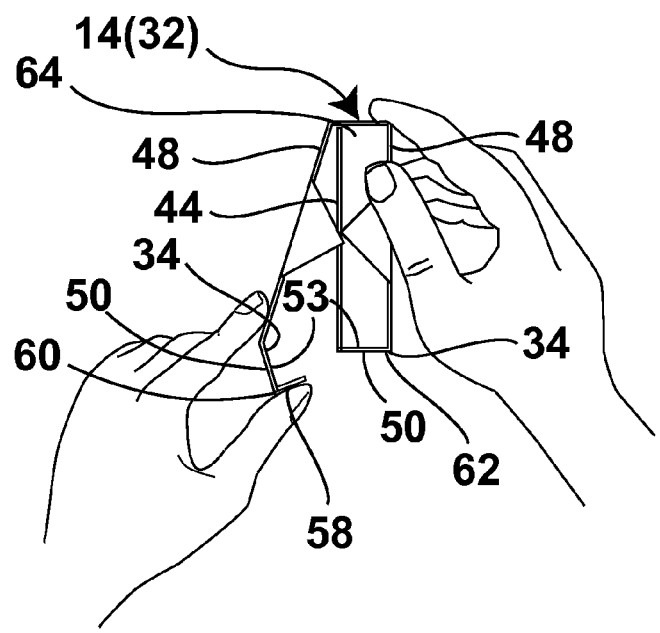
FIG. 4 is a diagrammatic side elevational view of the enclosure of the knockdownable, odorless, and smokeless vaporizer kit of the embodiments of the present invention shown in FIG. 3 and in the process of being further folded for assembly.

STEP 1: As shown in FIGS. 3 and 5A, fold the pair of second flaps 54 of the flat, planar, and isosceles triangular-shaped sheet 32 of the enclosure 14 in, along the pair of third weakened fold lines 56 of the flat, planar, and isosceles triangular-shaped sheet 32 of the enclosure 14, respectively, onto the pair of second sides 48 of the enclosure 14, respectively;

STEP 2: As shown in FIGS. 4 and 5B, fold the pair of second sides 48 of the enclosure 14, along the pair of first weakened fold lines 44 of the flat, planar, and isosceles triangular-shaped sheet 32 of the enclosure 14, towards each other until they are parallel to each other;

STEP 3: As shown in FIGS. 4 and 5B, fold the other first flap 50 of the flat, planar, and isosceles triangular-shaped sheet 32 of the enclosure 14 inwardly, along the base 34 of the flat, planar, and isosceles triangular-shaped sheet 32 of the enclosure 14, until it is perpendicular to an associated second side 48 of the enclosure 14;

STEP 4: As shown in FIGS. 4 and 5C, fold the third flap 58 of the flat, planar, and isosceles triangular-shaped sheet 32 of the enclosure 14 inwardly, along the fourth weakened fold line 60 of the flat, planar, and isosceles triangular-shaped sheet 32 of the enclosure 14;

STEP 5: As shown in FIGS. 4 and 5C, fold the one first flap 50 of the flat, planar, and isosceles triangular-shaped sheet 32 of the enclosure 14 inwardly, along the base 34 of the flat, planar, and isosceles triangular-shaped sheet 32 of the enclosure 14, until it overlies the other first flap 50 of the flat, planar, and isosceles triangular-shaped sheet 32 of the enclosure 14; and STEP 6: As shown in FIGS. 4 and 5D, insert the third flap 58 of the flat, planar, and isosceles triangular-shaped sheet 32 of the enclosure 14 into the through slot 62 of the flat, planar, and isosceles triangular-shaped sheet 32 of the enclosure 14 so as to form the third side 53 of the enclosure 14, and in so doing, converting the flat, planar, and isosceles triangular-shaped sheet 32 from the unfolded-not-in-use-mode thereof to the folded-in-use-mode thereof having an open bottom 64.

D. Method of Using the Knockdownable, Odorless, and Smokeless Vaporizer Kit 10.

Figure 6:
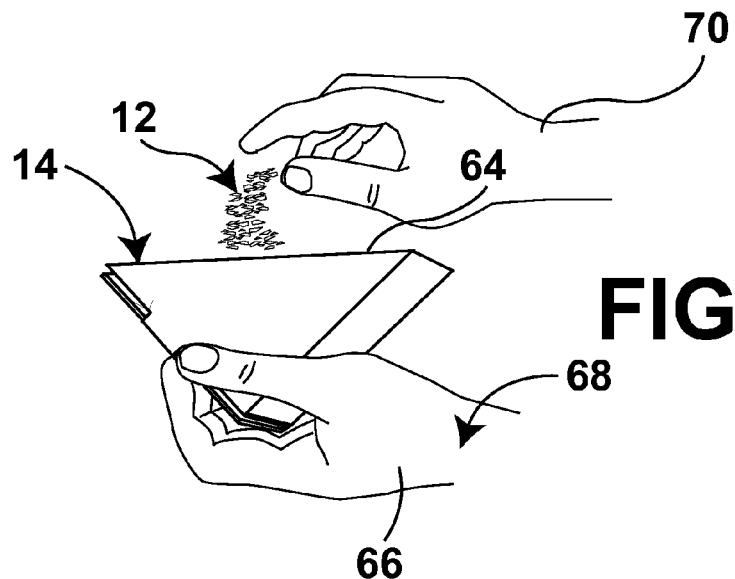
FIG. 6 is a diagrammatic perspective view of the assembled enclosure of the knockdownable, odorless, and smokeless vaporizer kit of the embodiments of the present invention receiving the material to be vaporized.

The method of using the knockdownable, odorless, and smokeless vaporizer kit 10 can best be seen in FIGS. 6, 7, 8, 9, and 10A-10C, which are, respectively, a diagrammatic perspective view of the assembled enclosure of the knockdownable, odorless, and smokeless vaporizer kit of the embodiments of the present invention receiving the material to be vaporized, a diagrammatic perspective view of the assembled enclosure of the knockdownable, odorless, and smokeless vaporizer kit of the embodiments of the present invention shown in FIG. 6 and being closed by a foil sheet of the knockdownable, odorless, and smokeless vaporizer kit of the embodiments of the present invention, a diagrammatic perspective view of the assembled enclosure of the knockdownable, odorless, and smokeless vaporizer kit of the embodiments of the present invention shown in FIG. 7 and having the foil sheet of the knockdownable, odorless, and smokeless vaporizer kit of the embodiments of the present invention folded around the enclosure of the knockdownable, odorless, and smokeless vaporizer kit of the embodiments of the present invention ready for use, an enlarged and exploded diagrammatic perspective view of the ready to use knockdownable, odorless, and smokeless vaporizer kit of the embodiments of the present invention being placed on a hot-plate heat source as shown in FIG. 1, and a flow chart of the method of using the knockdownable, odorless, and smokeless vaporizer kit, and as such, will be discussed with reference thereto.

The method of using the knockdownable, odorless, and smokeless vaporizer kit 10 comprises the steps of:

STEP 1: As shown in FIGS. 6 and 10A, hold the enclosure 14 in one hand 66 of a user 68, with the open bottom 64 of the enclosure 14 facing upwardly;

STEP 2: As shown in FIGS. 6 and 10A, deposit the material 12 by the other hand 70 of the user 68 into the enclosure 14, via the open bottom 64 of the enclosure 14;

STEP 3: As shown in FIGS. 7 and 10B, position the sheet of tin foil 18 by the other hand 70 of the user 68 on the open bottom 64 of the enclosure 14 to thereby close the open bottom 64 of the enclosure 14;

STEP 4: As shown in FIGS. 8 and 10B, wrap the sheet of tin foil 18 around the enclosure 14 so as to allow the sheet of tin foil 18 to be maintained on the enclosure 14 while closing the open bottom 64 of the enclosure 14;

STEP 5: As shown in FIGS. 9 and 10B, invert the enclosure 14; and

STEP 6: As shown on FIGS. 9 and 10C, apply the heat source 16 to the sheet of tin foil 18.

E. Impressions.

It will be understood that each of the elements described above or two or more together may also find a useful application in other types of constructions differing from the types described above.

While the embodiments of the present invention have been illustrated and described as embodied in a knockdownable, odorless, and smokeless vaporizer kit for vaporizing materials for inhalation without igniting the materials so as to reduce harmful effects of burning the materials by eliminating inhalation of combustion by-products of the materials by preventing ignition and combustion of the materials, however, they are not limited to the details shown, since it will be understood that various omissions, modifications, substitutions, and changes in the forms and details of the embodiments of the present invention illustrated and their operation can be made by those skilled in the art without departing in any way from the spirit of the embodiments of the present invention.

Without further analysis, the foregoing will so fully reveal the gist of the embodiments of the present invention that others can by applying current knowledge readily adapt them for various applications without omitting features that from the standpoint of prior art fairly constitute characteristics of the generic or specific aspects of the embodiments of the present invention.

The invention claimed is:

1. A knockdownable, odorless, and smokeless vaporizer kit for vaporizing materials for inhalation without igniting the materials so as to reduce harmful effects of burning the materials by eliminating inhalation of combustion by-products of the materials by preventing ignition and combustion of the materials, said kit comprising:
   a) an enclosure;
   b) a heat source; and
   c) a sheet of tin foil;
   wherein said enclosure is for containing the material;
   wherein said sheet of tin foil is attached to said enclosure; and wherein said sheet of tin foil interfaces with said heat source to heat said enclosure for vaporizing the materials contained within said enclosure without igniting the materials so as to reduce the harmful effects of burning the materials by eliminating inhalation of combustion by-products of the materials by preventing ignition and combustion of the materials;

wherein said enclosure has an unfolded-not-in-use-mode;

wherein said enclosure has a folded-in-use-mode;

wherein said enclosure in said unfolded-not-in-use-mode of said enclosure is a flat, planar, and isosceles triangular-shaped sheet;

wherein said flat, planar, and isosceles triangular-shaped sheet of said enclosure has:

a) a base
b) a pair of equal sides; and
c) a truncated apex;

wherein said base of said flat, planar, and isosceles triangular-shaped sheet of said enclosure is straight;

wherein said base of said flat, planar, and isosceles triangular-shaped sheet of said enclosure has a pair of ends;

wherein said truncated apex of said flat, planar, and isosceles triangular-shaped sheet of said enclosure is parallel to said base of said flat, planar, and isosceles triangular-shaped sheet of said enclosure;

wherein said truncated apex of said flat, planar, and isosceles triangular-shaped sheet of said enclosure is shorter than said base of said flat, planar, and isosceles triangular-shaped sheet of said enclosure;

wherein said truncated apex of said flat, planar, and isosceles triangular-shaped sheet of said enclosure has a pair of ends;

wherein a pair of first weakened fold lines depend from said pair of ends of said truncated apex of said flat, planar, and isosceles triangular-shaped sheet of said enclosure, respectively, to said base of said flat, planar, and isosceles triangular-shaped sheet;

wherein said pair of first weakened fold lines of said flat, planar, and isosceles triangular-shaped sheet of said enclosure define therebetween a first side of said enclosure when said enclosure is in said folded-in-use-mode thereof;

wherein said pair of first weakened fold lines of said flat, planar, and isosceles triangular-shaped sheet of said enclosure and said pair of equal sides of said flat, planar, and isosceles triangular-shaped sheet of said enclosure, respectively, define a pair of second sides of said enclosure when said enclosure is in said folded-in-use-mode thereof;

wherein said flat, planar, and isosceles triangular-shaped sheet of said enclosure has a pair of first flaps;

wherein said pair of first flaps of said flat, planar, and isosceles triangular-shaped sheet of said enclosure are rectangular-shaped;

wherein said pair of first flaps of said flat, planar, and isosceles triangular-shaped sheet of said enclosure depend coplanarly from said base of said flat, planar, and isosceles triangular-shaped sheet of said enclosure at a pair of second weakened fold lines;

wherein said pair of first flaps of said flat, planar, and isosceles triangular-shaped sheet of said enclosure extend from said pair of ends of said base of said flat, planar, and isosceles triangular-shaped sheet of said enclosure to said pair of first weakened fold lines of said flat, planar, and isosceles triangular-shaped sheet of said enclosure, respectively;

wherein said pair of first flaps of said flat, planar, and isosceles triangular-shaped sheet of said enclosure form a third side of said enclosure when said enclosure is in said folded-in-use-mode thereof;

wherein said flat, planar, and isosceles triangular-shaped sheet of said enclosure has a pair of second flaps;

wherein said pair of second flaps of said flat, planar, and isosceles triangular-shaped sheet of said enclosure are isosceles triangular-shaped;

wherein said pair of second flaps of said flat, planar, and isosceles triangular-shaped sheet of said enclosure extend coplanarly outwardly from said pair of equal sides of said flat, planar, and isosceles triangular-shaped sheet of said enclosure, respectively, at a pair of third weakened fold lines;

wherein said flat, planar, and isosceles triangular-shaped sheet of said enclosure has a third flap;

wherein said third flap of said flat, planar, and isosceles triangular-shaped sheet of said enclosure extends coplanarly outwardly from one of said first flaps of said flat, planar, and isosceles triangular-shaped sheet of said enclosure at a fourth weakened fold line;

wherein said flat, planar, and isosceles triangular-shaped sheet of said enclosure has a through slot; and wherein said through slot of said flat, planar, and isosceles triangular-shaped sheet of said enclosure extends along said base of said flat, planar, and isosceles triangular-shaped sheet of said enclosure at the other first flap of said flat, planar, and isosceles triangular-shaped sheet of said enclosure.

2. The knockdownable, odorless, and smokeless vaporizer kit of claim 1, further comprising mating portions of hook and loop fasteners.

3. The knockdownable, odorless, and smokeless vaporizer kit of claim 2, wherein said mating portions of hook and loop fasteners replaceably attach said heat source to said enclosure when said heat source is not in use.

4. The knockdownable, odorless, and smokeless vaporizer kit of claim 2, further comprising a secondary bag.

5. The knockdownable, odorless, and smokeless vaporizer kit of claim 4, wherein said secondary bag replaceably contains said mating portions of hook and loop fasteners when said mating portions of hook and loop fasteners are not in use.

6. The knockdownable, odorless, and smokeless vaporizer kit of claim 4, further comprising a primary bag.

7. The knockdownable, odorless, and smokeless vaporizer kit of claim 6, wherein said primary bag carries said enclosure, said heat source, said sheet of tin foil, and said secondary bag prior to assembling said knockdownable, odorless, and smokeless vaporizer kit.

8. The knockdownable, odorless, and smokeless vaporizer kit of claim 6, wherein said primary bag has a closure.

9. The knockdownable, odorless, and smokeless vaporizer kit of claim 8, wherein said closure of said primary bag is a pull cord.

10. The knockdownable, odorless, and smokeless vaporizer kit of claim 9, wherein said pull cord of said closure of said primary bag doubles as carrying handles.

11. The knockdownable, odorless, and smokeless vaporizer kit of claim 1, wherein said enclosure is more than one enclosure.

12. The knockdownable, odorless, and smokeless vaporizer kit of claim 1, wherein said sheet of tin foil is more than one sheet of tin foil.

13. The knockdownable, odorless, and smokeless vaporizer kit of claim 2, wherein said mating portions of hook and loop fasteners are more than one mating portions of hook and loop fasteners.

14. A method of using a knockdownable, odorless, and smokeless vaporizer kit, comprising the steps of:
   a) holding an enclosure of the knockdownable, odorless, and smokeless vaporizer kit in one hand of a user, with an open bottom of the enclosure facing upwardly;
   wherein said enclosure has an unfolded-not-in-use-mode;
   wherein said enclosure has a folded-in-use-mode;
   wherein said enclosure in said unfolded-not-in-use-mode of said enclosure is a flat, planar, and isosceles triangular-shaped sheet;
   wherein said flat, planar, and isosceles triangular-shaped sheet of said enclosure has:
   a) a base
   b) a pair of equal sides; and
   c) a truncated apex;
   wherein said base of said flat, planar, and isosceles triangular-shaped sheet of said enclosure is straight:
   wherein said base of said flat, planar, and isosceles triangular-shaped sheet of said enclosure has a pair of ends;
   wherein said truncated apex of said flat, planar, and isosceles triangular-shaped sheet of said enclosure is parallel to said base of said flat, planar, and isosceles triangular-shaped sheet of said enclosure;
   wherein said truncated apex of said flat, planar, and isosceles triangular-shaped sheet of said enclosure is shorter than said base of said flat, planar, and isosceles triangular-shaped sheet of said enclosure;
   wherein said truncated apex of said flat, planar, and isosceles triangular-shaped sheet of said enclosure has a pair of ends;
   wherein a pair of first weakened fold lines depend from said pair of ends of said truncated apex of said flat, planar, and isosceles triangular-shaped sheet of said enclosure, respectively, to said base of said flat, planar, and isosceles triangular-shaped sheet;
   wherein said pair of first weakened fold lines of said flat, planar, and isosceles triangular-shaped sheet of said enclosure define therebetween a first side of said enclosure when said enclosure is in said folded-in-use-mode thereof;
   wherein said pair of first weakened fold lines of said flat, planar, and isosceles triangular-shaped sheet of said enclosure and said pair of equal sides of said flat, planar, and isosceles triangular-shaped sheet of said enclosure, respectively, define a pair of second sides of said enclosure when said enclosure is in said folded-in-use-mode thereof;
   wherein said flat, planar, and isosceles triangular-shaped sheet of said enclosure has a pair of first flaps;
   wherein said pair of first flaps of said flat, planar, and isosceles triangular-shaped sheet of said enclosure are rectangular-shaped;
   wherein said pair of first flaps of said flat, planar, and isosceles triangular-shaped sheet of said enclosure depend coplanarly from said base of said flat, planar, and isosceles triangular-shaped sheet of said enclosure at a pair of second weakened fold lines;
   wherein said pair of first flaps of said flat, planar, and isosceles triangular-shaped sheet of said enclosure extend from said pair of ends of said base of said flat, planar, and isosceles triangular-shaped sheet of said enclosure to said pair of first weakened fold lines of said flat, planar, and isosceles triangular-shaped sheet of said enclosure, respectively;
   wherein said pair of first flaps of said flat, planar, and isosceles triangular-shaped sheet of said enclosure form a third side of said enclosure when said enclosure is in said folded-in-use-mode thereof;
   wherein said flat, planar, and isosceles triangular-shaped sheet of said enclosure has a pair of second flaps;
   wherein said pair of second flaps of said flat, planar, and isosceles triangular-shaped sheet of said enclosure are isosceles triangular-shaped;
   wherein said pair of second flaps of said flat, planar, and isosceles triangular-shaped sheet of said enclosure extend coplanarly outwardly from said pair of equal sides of said flat, planar, and isosceles triangular-shaped sheet of said enclosure, respectively, at a pair of third weakened fold lines;
   wherein said flat, planar, and isosceles triangular-shaped sheet of said enclosure has a third flap;
   wherein said third flap of said flat, planar, and isosceles triangular-shaped sheet of said enclosure extends coplanarly outwardly from one of said first flaps of said flat, planar, and isosceles triangular-shaped sheet of said enclosure at a fourth weakened fold line;
   wherein said flat, planar, and isosceles triangular-shaped sheet of said enclosure has a through slot; and
   wherein said through slot of said flat, planar, and isosceles triangular-shaped sheet of said enclosure extends along said base of said flat, planar, and isosceles triangular-shaped sheet of said enclosure at the other first flap of said flat, planar, and isosceles triangular-shaped sheet of said enclosure;
   b) depositing material by the other hand of the user into the enclosure, via the open bottom of the enclosure;
   c) positioning a sheet of tin foil by the other hand of the user on the open bottom of the enclosure to thereby close the open bottom of the enclosure;
   d) wrapping the sheet of tin foil around the enclosure so as to allow the sheet of tin foil to be maintained on the enclosure while closing the open bottom of the enclosure;
   e) inverting the enclosure; and
   f) applying a heat source to the sheet of tin foil.

* * * * *